(12) United States Patent
Crunaire et al.

(10) Patent No.: US 8,759,111 B2
(45) Date of Patent: Jun. 24, 2014

(54) NANOPOROUS DETECTORS OF MONOCYCLIC AROMATIC COMPOUNDS AND OTHER POLLUTANTS

(75) Inventors: Sabine Crunaire, Douai (FR); Thu-Hoa Tran-Thi, St. Fargeau-ponthierry (FR)

(73) Assignees: CEA—Commisariat a l'Energie Atomique et aux Energies Alternatives, Paris (FR); CNRS—Centre National de la Recherche Scientifique, Paris (FR)

( * ) Notice: Subject to any disclaimer, the term of this patent is extended or adjusted under 35 U.S.C. 154(b) by 609 days.

(21) Appl. No.: 13/003,461

(22) PCT Filed: Jul. 10, 2009

(86) PCT No.: PCT/FR2009/051376
§ 371 (c)(1),
(2), (4) Date: Mar. 4, 2011

(87) PCT Pub. No.: WO2010/004225
PCT Pub. Date: Jan. 14, 2010

(65) Prior Publication Data
US 2011/0151573 A1  Jun. 23, 2011

(30) Foreign Application Priority Data
Jul. 11, 2008 (FR) ...................................... 0854755

(51) Int. Cl.
*G01N 33/00* (2006.01)
*G01N 1/18* (2006.01)
*C03B 19/12* (2006.01)
*B01J 20/10* (2006.01)
*B01J 20/26* (2006.01)
*B01J 20/28* (2006.01)
*C08L 83/08* (2006.01)

(52) U.S. Cl.
CPC .................. *C08L 83/08* (2013.01); *C03B 19/12* (2013.01); *B01J 20/10* (2013.01); *B01J 20/26* (2013.01); *B01J 20/28047* (2013.01); *B01J 20/2808* (2013.01)

USPC ........... 436/130; 436/127; 436/128; 436/129; 436/139; 436/140; 436/141; 436/142; 436/164; 436/167; 436/172; 436/177; 436/178

(58) Field of Classification Search
USPC ......... 436/127–130, 139–142, 164, 167, 172, 436/177–178
See application file for complete search history.

(56) References Cited

U.S. PATENT DOCUMENTS

| 4,017,528 | A | 4/1977 | Unger et al. |
| 4,436,823 | A | 3/1984 | Bümcke et al. |

(Continued)

FOREIGN PATENT DOCUMENTS

| EP | 1 566 213 | 8/2005 |
| EP | 1 712 889 | 10/2006 |

(Continued)

OTHER PUBLICATIONS

Abstract for FR 2 890 745 which was also filed as US 2008/0220534.

(Continued)

*Primary Examiner* — Arlen Soderquist
(74) *Attorney, Agent, or Firm* — Frost Brown Todd LLC

(57) ABSTRACT

Porous sol-gel material essentially consisting of units of one or more first polyalkoxysilanes chosen from the following compounds: (chloromethyl)triethoxysilane; 1,3-dimethyltetramethoxydisiloxane; ethyl trimethoxysilane; triethoxy(ethyl)silane; triethoxymethylsilane; triethoxy(vinyl)silane; trimethoxymethylsilane; trimethoxy(vinyl)silane; tetraethoxysilane or tetramethoxysilane (TMOS) and of units of one or more second polyalkoxysilanes chosen from the following compounds: (N-(3-(trimethoxysilyl)propyl)ethylenediamine; 3-aminopropyltriethoxysilane (APTES) and 3-aminopropyltrimethoxysilane, in a first polyalkoxysilane/second polyalkoxysilane molar ratio of 1/0.01 to 1/1, optionally comprising a probe molecule, method of preparation and applications in the trapping of monocyclic aromatic hydrocarbons and other pollutants or in their detection.

34 Claims, 6 Drawing Sheets

(56) References Cited

U.S. PATENT DOCUMENTS

| | | | | |
|---|---|---|---|---|
| 4,857,395 | A | * | 8/1989 | Benton et al. ............... 428/306.6 |
| 5,114,760 | A | * | 5/1992 | Takemura et al. ......... 427/430.1 |
| 5,244,813 | A | * | 9/1993 | Walt et al. ..................... 436/172 |
| 5,468,606 | A | * | 11/1995 | Bogart et al. ..................... 435/5 |
| 5,501,836 | A | * | 3/1996 | Myerson ........................... 422/400 |
| 6,235,532 | B1 | * | 5/2001 | Uttamchandani et al. ...... 436/60 |
| 6,251,989 | B1 | * | 6/2001 | Edelmann et al. ............ 524/837 |
| 6,310,110 | B1 | * | 10/2001 | Markowitz et al. ............. 521/99 |
| 6,387,453 | B1 | * | 5/2002 | Brinker et al. ................ 427/387 |
| 6,667,016 | B1 | | 12/2003 | Meyer et al. |
| 6,747,123 | B2 | * | 6/2004 | Chen et al. .................... 528/480 |
| 6,756,217 | B1 | * | 6/2004 | Dave et al. .................... 435/176 |
| 6,783,680 | B2 | * | 8/2004 | Malik ........................... 210/635 |
| 6,850,356 | B2 | * | 2/2005 | Kawahara et al. ............ 359/296 |
| 6,855,335 | B2 | * | 2/2005 | Seok et al. .................... 424/489 |
| 7,563,451 | B2 | * | 7/2009 | Lin et al. ....................... 424/400 |
| 7,595,350 | B2 | * | 9/2009 | Xu ................................. 516/111 |
| 7,618,608 | B1 | * | 11/2009 | Keller, Sr. ..................... 423/338 |
| 7,674,631 | B2 | * | 3/2010 | Pawliszyn ..................... 436/178 |
| 7,776,611 | B2 | * | 8/2010 | Crudden et al. ............. 436/171 |
| 2002/0150923 | A1 | * | 10/2002 | Malik ............................... 435/6 |
| 2003/0175534 | A1 | * | 9/2003 | Chen et al. .................... 428/447 |
| 2003/0180964 | A1 | | 9/2003 | Yang et al. |
| 2003/0231984 | A1 | | 12/2003 | Bright et al. |
| 2004/0256748 | A1 | * | 12/2004 | Seok et al. ..................... 264/4.1 |

FOREIGN PATENT DOCUMENTS

| | | |
|---|---|---|
| FR | 2 890 745 | 3/2007 |
| WO | WO 2006/094392 | 9/2003 |

OTHER PUBLICATIONS

Calvo-Munoz, M.L et al., "Chemical sensors of monocyclic aromatic hydrocarbons based o sol-gel materials: kinetics of trapping of the pollutants and sensitivity of the sensor," Sensors and Actuators B, vol. 87(1) (Nov. 15, 2002) pp, 173-183 (Abstract only).

Kunzelmann, U. et al., "Biosensor properties of glucose oxidase immobilized within $SiO_2$ gels," Sensors and Actuators B: Chemical, vol. 38 (1-3) (Mar.-Apr. 1997) pp. 222-228 (Abstract only).

Calvo-Muñoz, M.L. et al., "Chemical sensors of monocyclic aromatic hydrocarbons based on sol-gel materials: synthesis, structural characterization and molecular interactions," J. Mater. Chem., vol. 12 (2002) pp. 461-467.

Janotta, M. et al., "Sol-Gel-Coated Mid-Infrared Fiber-Optic Sensors," Applied Spectroscopy, vol. 57(7) (2003) pp. 823-828.

Scharnweber, T. et al., "Application of Sol-Gel Glass Immunoadsorbers for the Enrichment of Polycyclic Aromatic Hydrocarbons (PAHs) from Wet Precipitation," Filed Analytical Chemistry and Technology, vol. 4(1) (2000) pp. 43-52.

* cited by examiner

NANOPOROUS DETECTORS OF MONOCYCLIC AROMATIC COMPOUNDS AND OTHER POLLUTANTS

The present invention relates to nanoporous detectors of monocyclic aromatic compounds and other compounds (aldehydes, alkanes, carboxylic acids and ketones), and to the uses thereof.

Monocyclic aromatic compounds are for the most part toxic atmospheric pollutants and, for benzene, even carcinogenic. They are found in environments such as the petrochemical industry, in the chemical industry (use of solvents), in environments close to industrial plants, in professional environments (research laboratories, analytical laboratories, etc.), in car fuels and in ambient air (evaporation of fuels, incomplete combustion of fossil energy, smoking, use of household maintenance products or do-it-yourself products).

For issues of monitoring atmospheric pollution in polluted atmospheres or of surveilling workers directly exposed to these compounds, it is necessary to detect and quantify the most volatile aromatic products, commonly known as BTEXMs (Benzene, Toluene, Ethylbenzene, Xylenes (ortho, meta and para), trimethyl(1,2,3; 1,2,4 and 1,3,5)-benzenes).

Measurements of Monocyclic Aromatic Hydrocarbons (MAH) are usually performed in ambient air and in indoor air:

These measurements are performed in two distinct steps: sampling and then analysis. At work premises, two types of measurement are performed: either individual exposure of the staff, or measurement of ambience around a fixed working point. The sampling may be either active (pumping of the air through a cartridge of silica covered with a stationary phase) or passive (by diffusion through the same cartridge without pumping). In both cases, the analysis is performed at a later stage in the laboratory.

For sampling followed by an in-situ analysis, continuous analyzers exist. Mention may be made of portable microchromatographs operating autonomously (sampling, concentration, analysis). However, they are bulky and require the use of various gases, nitrogen, air and hydrogen with an FID detector (flame ionization detector) or nitrogen with a PID detector (photoionization detector), the latter being limited to concentrations of less than 300 ppbv (parts per billion by volume).

To satisfy the demand for direct-measurement detectors, many researchers have sought to develop chemical sensors for BTEXMs with good selectivity.

The difficulty in finding specific probe molecules for these compounds arises from the fact that they are virtually apolar (dipolar moments ranging between 0 and 0.3 Debye). BTEXMs can therefore interact only weakly with other molecules via short-range electrostatic forces or dispersion forces. The detection principles reported in the literature are essentially based on these unselective weak interactions and on size-based selectivity tests. Aromatic macrocycles, fluorophores that are sensitive to the microscopic environment such as Nile Red, and sensors based on semiconductors and mixed oxides, are used for this purpose. For a size-based selectivity, cage molecules whose cavity is sized so as to receive the target pollutant (example: paracyclophanes, calixarenes or cyclodextrins) have been proposed, but these systems are not selective.

Benzene detectors based on porous matrices of organic-inorganic hybrid polymers based on silicon alkoxides ($Si(OR)_nR_{4-n}$ with $R=CH_3$) are also known. Using matrices with a thickness that may range between 500 µm and 2 mm, and having nanopores with a radius of between 3.5 and 9 Å, Calvo-Muñoz et al. ("Chemical sensors of monocyclic aromatic hydrocarbons based on sol-gel materials: kinetics of trapping of the pollutants and sensitivity of the sensor", Sensors and Actuators B, vol. 87, pp. 173-183, 2002) have shown that it is possible to virtually irreversibly trap benzene and toluene and to discriminate between them by means of their absorption spectrum. With monolithic blocks 2 mm thick, the sensitivity obtained in the laboratory for benzene and toluene is 10 ppbv, for an exposure of 2 hours at a throughput of 20 $mL \cdot min^{-1}$. For higher exposure throughputs of 250 $mL \cdot min^{-1}$, 60 ppbv may be measured in an exposure time of 14 minutes. The trapping yield for benzene and toluene in these matrices is 100% for low concentrations (<10 ppbv) and low throughput (20 $mL \cdot min^{-1}$) but decreases greatly (5 to 6%) when the concentration is >1 ppmv (parts per million by volume) and when the throughput is >50 $mL \cdot min^{-1}$. In all cases, the trapping is virtually irreversible. Ortho-Xylene and meta-xylene and also trimethylbenzenes cannot diffuse in these materials, whose pores are too small (diameter <20 Å), which makes them selective detectors for benzene, toluene and para-xylene only. Even though the trapping and measurement are performed in a single step, the trapping of pollutants is, however, irreversible.

Since 2001, the company NTT (Nippon Telegraph & Telephone Corp.) has been working on various porous adsorbents in the form of silica cubes with a diameter of about 2 µm, with controlled pore sizes, which serve for trapping BTEMXs. See, for example, Ueno Y., A. Tate, and O. Niwa "Benzene sensor and method for manufacturing same", patent EP 1 712 889 A1, 18 Oct. 2006. The cubes fill a microfluidic flow chamber equipped with a heating system (electrical resistance etched on the rear face) which serves for thermal desorption of the pollutants. During the preconcentration step, the air containing the pollutants is pumped through the flow chamber for a time from a few tens of minutes to 1 hr 30 minutes depending on the content of pollutants. These pollutants are partially trapped in the porous material. The chamber is then heated at 200° C. for 10 seconds to desorb the pollutants. The gases are transferred via a second pump into an optical chamber (2 cm quartz cell or 12 cm optical fiber) and are detected by means of their absorbance using a UV spectrophotometer (Soma Optics, Fastevert S-2400). The selectivity is obtained by spectral deconvolution from a spectral databank of the various BTEMXs. The combined trapping and detection device is included in a ventilated case 37.5×20×16 cm in size weighing 6.7 kg, computer not included. The sensitivity of the detector is 1 ppbv for 90 minutes of exposure, or 50 ppbv for 50 minutes of exposure. The detector is sparingly sensitive to the relative humidity of the air between 40% and 80% relative humidity.

The apparatus from the company NTT has the required criteria in terms of sensitivity and speed, but the device still involves two steps, namely preconcentration and analysis. In this case, a heating system with a rapid temperature ramp is necessary to expel the pollutants trapped in these matrices and to transfer them into the analysis chamber.

From examination of the analyzers sold or proposed in the literature, it appears that there is a demand for devices that allow the trapping and measurement of Monocyclic Aromatic Hydrocarbons (MAH) in a single step, while maintaining the reversible nature of the process. Preferably, a single chamber would be used for the exposure to MAHs and for measuring them. It would also be desirable to be able to desorb the gases without the need for a heating device.

The sensor production steps should be as short as possible, for example less than 24 hours.

The size and cost of manufacturing the sensors should be as small as possible.

The material of the sensors should allow rapid diffusion of the pollutants and show a good MAH trapping yield.

The trapping should be reversible.

The detection system using such sensors should be able to be miniaturized while maintaining a good signal/noise ratio.

For measurements at a work premises, it would also be desirable for a detection system to have good autonomy, for example at least 8 hours, which corresponds to one working day, and for it to be robust, sparingly bulky, easily transportable by an individual, and thus light.

Now, after considerable research, the Applicant has discovered a polyvalent detector of BTEMXs and of their usual solvents, based on the use of novel porous materials, which is satisfactory.

Consequently, the subject of the present patent application is a porous sol-gel material essentially formed from
  units of one or more first polyalkoxysilane(s) chosen from the following compounds: (chloromethyl)triethoxysilane; 1,3-dimethyltetramethoxydisiloxane; ethyltrimethoxysilane; triethoxy(ethyl)silane; triethoxymethylsilane; triethoxy(vinyl)silane; trimethoxymethylsilane; trimethoxy(vinyl)silane; tetraethoxysilane or tetramethoxysilane and advantageously only one polyalkoxysilane and more particularly tetramethoxysilane (TMOS), and
  units of one or more second polyalkoxysilane(s) chosen from the following compounds: (N-(3-(trimethoxysilyl)propyl)ethylenediamine; 3-amino-propyltriethoxysilane (APTES) and 3-aminopropyltrimethoxysilane and advantageously 3-aminopropyltriethoxysilane, in a first polyalkoxy-silane(s)/second polyalkoxysilane(s) mole ratio from 1/0.01 to 1/1, preferably from 1/0.01 to 1/0.50, especially from 1/0.01 to 1/0.30, particularly from 1/0.01 to 1/0.15, most particularly from 1/0.02 to 1/0.06; preferably the first polyalkoxysilane is TMOS.

It should be noted that (N-(3-(trimethoxysilyl)propyl)ethylenediamine, 3-aminopropyltriethoxysilane (APTES) and 3-aminopropyltrimethoxysilane comprise at least one primary amine function.

The first polyalkoxysilane(s) are especially chosen from the following compounds: methyltrimethoxysilane, tetraethoxysilane, methyltriethoxysilane and tetramethoxysilane (TMOS).

Preferably, the porous sol-gel material is essentially formed from units of one or more first polyalkoxysilane(s) and units of a single second polyalkoxysilane, and particularly units of a single first polyalkoxysilane and units of a single second polyalkoxysilane.

A subject of the present application is also a sol-gel material that may be prepared essentially from one or more first polyalkoxysilane(s) chosen from the following compounds: (chloromethyl)triethoxysilane; 1,3-dimethyltetramethoxydisiloxane; ethyltrimethoxysilane; triethoxy(ethyl)silane; triethoxymethylsilane; triethoxy(vinyl)silane; trimethoxymethylsilane; trimethoxy(vinyl)silane; tetraethoxysilane or tetramethoxysilane and advantageously a single polyalkoxysilane and more particularly tetramethoxysilane (TMOS) and units of one or more second polyalkoxysilane(s) chosen from the following compounds: (N-(3-(trimethoxysilyl)propyl)ethylenediamine; 3-aminopropyltriethoxysilane (APTES) and 3-aminopropyltrimethoxysilane and advantageously 3-aminopropyltriethoxysilane, in a first polyalkoxysilane(s)/second polyalkoxysilane(s) mole ratio from 1/0.01 to 1/1, preferably from 1/0.01 to 1/0.50, especially from 1/0.01 to 1/0.30, particularly from 1/0.01 to 1/0.15 and most particularly from 1/0.02 to 1/0.06; preferably, the first polyalkoxysilane is TMOS.

Porous sol-gel materials that can be prepared essentially from one or more first polyalkoxysilane(s) and from a single second polyalkoxysilane, and particularly from a single first polyalkoxysilane and a single second polyalkoxysilane, are preferred.

The preparation methods are outlined hereinbelow.

The sol-gel material of the invention is porous and it has a pore size distribution ranging from 10 to 60 angstroms, and especially from 20 to 60 angstroms, and a specific surface area of from 200 to 800 $m^2 \cdot g^{-1}$. Preferentially, the specific surface area is $650 \pm 70$ $m^2 \cdot g^{-1}$.

Among the second polyalkoxysilanes included in the composition of the material, 3-aminopropyltriethoxysilane (APTES) is preferred.

Particularly preferred sol-gel materials are prepared essentially from tetramethoxysilane (TMOS) and 3-aminopropyltriethoxysilane (APTES) in a TMOS/APTES mole ratio from 1/0.01 to 1/0.30, preferably from 1/0.01 to 1/0.15, advantageously from 1/0.01 to 1/0.10, especially from 1/0.02 to 1/0.06 and most particularly of 1/0.03, and thus comprise units of one and the other in such proportions.

As a reminder, a sol-gel material is a material obtained via a sol-gel process that consists in using as precursors alkoxides of formula $M(OR)_n$ in which M is a metal, especially silicon, and R is an alkyl group, and in hydrolyzing them. In the presence of water, the hydrolysis of the alkoxy groups (OR) takes place, forming small particles generally less than 1 nanometer in size. These particles aggregate and form lumps that remain in suspension without precipitating, and form a sol. Increasing the lumps increases the viscosity of the medium which gels. A sol-gel material is obtained by drying the gel, by removing the solvent from the polymer network formed.

The sol-gel material of the invention comprises units and is essentially prepared from 2 to 4 polyalkoxysilanes, especially 2 or 3 and particularly 2 polyalkoxysilanes. The final material may contain from 50% to 95% of polyalkoxysilane derivatives.

Structuring compounds (organic polymers, neutral surfactants, anionic surfactants, cationic surfactants, etc.), which allow the production of a regular porous structure and/or particular cavity shapes, may be added to the starting sol provided that they can be removed by washing or calcination without deteriorating the optical and structural properties of the matrix.

A subject of the present patent application is also a sol-gel material hereinabove incorporating a probe molecule.

Whether or not it is specified, in the text hereinbelow, the term "sol-gel material" denotes both a sol-gel material alone and a sol-gel material incorporating a probe molecule, except when the context shows that it is one of them and not the other.

A probe molecule is a molecule that is suited to the compounds or pollutants to be trapped or detected or trapped and detected, with which it may react, and may be, for example, 4-amino-3-penten-2-one (Fluoral-P®) for the detection of formaldehyde. The incorporation of a probe molecule makes it possible to broaden the range of compounds or pollutants targeted by the invention.

Preferred probe molecules are hydralazine for the detection of acetaldehyde, hexyldehyde and crotonaldehyde; 2,4-dinitrophenylhydrazine for the detection of aldehydes and ketones as a whole; 4-amino-3-penten-2-one (Fluoral-P®) for the detection of formaldehyde, iodine oxides ($KIO_4$, $I_2O_4$ and $I_2O_5$) for aromatic compounds or alkanes, a triphenylmethane derivative (bromothymol blue, bromophenol blue, bromocresol green, cresol red, phenolphthalein, malachite green, etc.) or an azobenzene derivative (helianthin, Congo red, methyl red, methyl yellow, alizarin yellow R, etc.) for the detection of carboxylic acids.

The weight percentage of probe molecules is advantageously from 0.1% to 40%, preferably from 10% to 40% and most particularly from 10% to 30% relative to the total weight of the material.

A subject of the present patent application is also a process for preparing a sol-gel hereinabove, characterized in that the first polyalkoxysilane(s), preferably tetramethoxysilane, are mixed with a water-miscible organic solvent therefor, the second polyalkoxysilane(s) are then added, water is added, supplemented, if desired, with a catalyst or a structuring agent, or both, and stirring is continued to obtain the sol and then the gel. If desired, the sol is placed in molds to obtain blocks of the gel. In combined form, the tetramethoxysilane and second polyalkoxysilane molecules are known as "units".

Advantageously, the first polyalkoxysilane(s) are mixed at a temperature between −45 and +30° C. with a water-miscible organic solvent therefor, the second polyalkoxysilane(s) are then added, water is added, supplemented, if desired, with a catalyst or a structuring agent, or both, and preferably only a structuring agent, and stirring is continued to obtain the sol and then the expected sol-gel, and according to an advantageous mode, the sol is placed in molds to obtain blocks of the expected sol-gel.

It should be noted that, in the present patent application, the indefinite article "a" should conventionally be considered as a generic plural (meaning "at least one" or "one or more"), except where the context shows otherwise (1 or "a single"). Thus, for example, when it is stated hereinabove that a structuring agent is added, it is a case of adding one or more structuring agents, or when it is stated that a probe molecule is incorporated, it is a case of adding one or more probe molecules.

Under preferential conditions of implementation of the process described above, the first polyalkoxysilane(s), preferably tetramethoxysilane (TMOS), are mixed with an organic solvent therefor, which is especially acetone, formamide, methyl ethyl ketone, chloroform, dichloromethane, acetic acid, methanol, ethanol, propanol, butanol, pentanol or hexanol, and preferably an alcohol, especially a $C_1$-$C_5$ and advantageously $C_1$-$C_3$ alkanol and in particular methanol.

The mixing may be performed at a temperature of between −45 and +30° C. and preferably between −25 and −15° C., for a time of between 1 and 10 minutes and preferentially from 2 to 3 minutes. Advantageously, the mixing is performed at a temperature between −25 and −15° C. for a time of between 2 and 3 minutes.

The second polyalkoxysilane(s) and most particularly 3-(aminopropyl)triethoxysilane are then added, preferably in a proportion less than or equal to the first. Stirring is continued for a time generally from 1 to 10 minutes and preferentially from 2 to 3 minutes. To finish, the water added is preferably ultrapure, supplemented, if need be, with catalyst and/or structuring agent, and preferably only with a structuring agent. Stirring is then continued for a further 10 to 120 seconds and more particularly for a further 40 to 60 seconds.

Preferably, all the above synthetic steps are performed at low temperature.

The polyalkoxysilanes/solvent/water mole ratio is advantageously from 1/4/1 to 1/100/30, particularly 1/4/4 and most particularly 1/5/4.

Polystyrene or polypropylene is advantageously used as constituent material of the molds to obtain the expected gel blocks.

Under other preferential conditions for performing the process described above, the sol-gel blocks are also dried so as to evaporate off the residual solvents. Drying of the sol-gel matrices advantageously proceeds at a controlled temperature and under an atmosphere of dry inert gas (nitrogen, argon, air, etc.). The drying of the sol-gel blocks may especially be performed by placing a gas-permeable cover and more particularly a porous film at the surface of the molds, followed by placing these molds in a thermostatically regulated chamber at a temperature of between 25 and 60° C. and more particularly at 45° C. in the case of a material not incorporating any probe molecules and at 25° C. in the opposite case. The drying atmosphere will preferentially be a dry, pure inert gas (U-grade nitrogen, FID-grade industrial air, etc.). The duration for complete drying will be variable between 2 hours and 10 days, and in the preferential case about 2 hours for a block with a volume of about $2\times10^{-3}$ or especially $5\times10^{-3}$ cm$^3$.

When the material contains one or more surfactants, these surfactants are removed either by washing or dipping in an aqueous or organic solution or alternatively by calcination, after gelation.

A subject of the present application is also a process for preparing a sol-gel material incorporating a probe molecule that is capable of selectively reacting with a target compound. The incorporation of this or these probe molecules may be performed according to several methods:

the "one-pot" method, which is the preferred method, which consists in adding the probe molecule directly during the preparation of the sol. In this case, the probe molecule is directly encapsulated in the silica network. Dilution or dissolution of the probe molecules may take place either in the solvent or in the water serving for the preparation of the sol. The preferential choice will be to dilute or dissolve the probe molecule in the medium in which it is the most soluble or the most miscible.

The gas-phase or liquid-phase diffusion method consists in including the probe molecule in the empty pores of the sol-gel material after it has been dried. In this case, the probe molecules are adsorbed onto the surface of the material or bound to this surface by non-covalent bonds (hydrogen bonds or ionic bonds). The gas-phase diffusion method consists in placing the probe molecules in contact in gaseous form directly with the material (under partial vacuum or with circulation of the gas). The liquid-phase diffusion method consists in placing the sol-gel material directly in a solution (aqueous or solvent) containing the dissolved or diluted probe molecule.

The functionalization or post-doping method, which consists in creating a covalent bond between the sol-gel material and the probe molecule. To do this, it is advantageous to functionalize the surface of the sol-gel material in order to improve its compatibility with the probe molecule or to functionalize said molecule.

As has been seen, two or more probe molecules may be incorporated.

The sol-gel materials that are the subject of the present invention have very advantageous properties and qualities. They are especially endowed with noteworthy properties of trapping a whole variety of common solvents and of monocyclic aromatic hydrocarbons and especially benzene, toluene, xylenes, mesitylene and styrene.

They are also UV-transparent, which makes it possible directly to measure the absorbance of the trapped monocyclic aromatic hydrocarbons, these hydrocarbons generally being distinguished by their UV absorbance.

The sol-gel materials that are the subject of the present invention may be used with monocyclic aromatic hydrocarbons especially in gaseous form.

More generally, the sol-gel materials of the invention can trap compounds that absorb in the UV-visible range with a molar extinction coefficient of greater than 250 $M^{-1}cm^{-1}$. The sensitivity is suitable for concentrations ≥1 ppmv and even for about 10 ppbv for gases with a high absorption coefficient, such as styrene.

They allow the detection of BTEMXs directly via an absorbance measurement. In certain cases, such as in the case of styrene, metrology of the pollutant may also be performed by means of fluorescence measurements.

When used in a low thickness, for example from 100 to 800 µm and advantageously from 100 to 500 µm, they allow reversible trapping of MAHs and of their usual solvents.

The use of a spectrophotometer, advantageously miniaturized and cooled, allows detection by absorbance or fluorescence measurement that is of excellent quality and is sensitive.

When compared with porous adsorbents in the form of silica cubes, the following advantages may be noted in particular:
 trapping and measurement are possible in a single step;
 a single chamber serves for the exposure and the measurement;
 the desorption of the gases may be performed without heating, by using a millifluidic system suited to the sensor.

By virtue especially of the use of two different groups of polyalkoxysilanes, first and second polyalkoxysilanes as defined previously, relative to benzene adsorbents based on porous matrices of organic-inorganic hybrid polymers based on silicon alkoxides ($Si(OR)_nR_{4-n}$ with R=$CH_3$), the following advantages may be noted in particular:
 the synthetic and drying steps for the porous sensors are reduced to 4 hours instead of 2 months;
 the size of the sensors and their manufacturing cost are reduced;
 the new porous material allows faster diffusion of the target compounds;
 the millifluidic system allows an increase in the trapping yield;
 the trapping is reversible and the target compounds are desorbed without heating;
 the detection system can be miniaturized and the signal/noise ratio is improved.

Moreover, the sol-gel materials that are the subject of the present invention allow long autonomy of 300 to 400 measurements, which would correspond to 3 to 4 days if one measurement is performed every 15 minutes. This autonomy can be increased to 6 to 8 days if the measuring rate becomes equal to 30 minutes and even longer if the measuring rate decreases; in addition, trapping devices and/or detection systems using them are robust, of low bulk, portable and light.

The sol-gel materials that are the subject of the present invention have the property of having an intrinsic pH close to 7. By virtue of the use of the various abovementioned amino polyalkoxides, it is possible to modify the intrinsic pH of the material without the need to add a base ($OH^-$). The pH values are between 7 and 8.2. In the abovementioned preferential case, the pH is equal to 7.5±0.3.

When they incorporate a probe molecule, the matrices may selectively trap a whole variety of compounds by means of a specific reaction between the probe molecule and the target compound. In this case, the trapping of the analyte (target compound) is irreversible. The trapped target compound can then be measured quantitatively by detecting the product derived from the interaction or from the reaction thereof with the probe molecule. The other target compounds present in the medium at the time of the analysis may also be trapped in this case, but are not detected in the absence of a specific reaction. In other cases, the probe molecules are sensitive to small pH variations due to the trapping of an acidic target compound, which interacts via weak bonds with the probe molecule. In this case, the reaction is reversible.

These properties are illustrated below in the experimental section. They justify the use of the sol-gel materials described above, and also of the sol-gel materials incorporating a probe molecule, in the trapping of monocyclic aromatic hydrocarbons, and also other target compounds and/or in their detection.

Consequently, a subject of the present patent application is also a process for trapping monocyclic aromatic hydrocarbons or other compounds of interest using, as sensor, a sol-gel material described above, in which a stream that may contain monocyclic aromatic hydrocarbons or other target molecules is placed in contact with a sol-gel material described above, optionally incorporating a probe molecule, or such a stream is made to circulate thereon.

The stream that may contain monocyclic aromatic hydrocarbons may originate from a polluted atmosphere. It may circulate at a throughput of 10 $mL·min^{-1}$ to 1.1 $L·min^{-1}$.

A subject of the present patent application is also a process for preparing a sol-gel material incorporating an above probe molecule, characterized in that a probe molecule is added to the sol-gel material either directly during the preparation of the sol of the sol-gel material or by diffusion of this probe molecule into said material via gas-phase or liquid-phase diffusion.

A subject of the present patent application is also a process for preparing a sol-gel material incorporating one or more probe molecules mentioned above, characterized in that the probe molecule(s) are added to the sol-gel material, at a low temperature of −45 to +15° C., either directly during the preparation of the sol of the sol-gel material or by diffusion of this or these probe molecule(s) in said material via gas-phase or liquid-phase diffusion. The sol-gel material has an intrinsic pH close to 7, which may be varied within a pH range from 7 to 8.2, and for example, when the first alkoxysilane unit is TMOS and the second polyalkoxysilane unit is APTES, by increasing the proportion of APTES relative to the TMOS.

In addition to trapping monocyclic aromatic hydrocarbons, it is also possible to detect and/or assay them. To this end, trapping of these molecules may also be performed.

A subject of the present patent application is thus also an above process in which, in addition, monocyclic aromatic hydrocarbons and common solvents therefor trapped in the above sol-gel materials, optionally incorporating a probe molecule, are detected.

The detection may be performed especially by optical, mass or acoustic measurements.

When the detection is performed by optical measurement, the wavelength for which the absorbance of the target compound is the highest is preferably chosen. The wavelength for which the fluorescence of the target compound is the highest may also be chosen.

To assay the monocyclic aromatic hydrocarbons trapped on the above sol-gel materials, optionally incorporating a probe molecule, it is especially possible to perform a measurement of absorbance, fluorescence, luminescence, mass or resonance frequency variation of the monolith when it is exposed to a stream containing the target compound(s). The measurement obtained, compared with the measurement obtained from calibrated streams of target compound, directly gives information regarding the amount and/or nature of the target compound contained in the exposure stream.

As has been seen above, when they incorporate a probe molecule, the above sol-gel materials can trap a whole variety of target compounds, such as monocyclic aromatic compounds, aldehydes, alkanes, carboxylic acids, ketones and chlorine, especially monocyclic aromatic compounds, aldehydes, alkanes, carboxylic acids and ketones.

Consequently, a subject of the present patent application is also a process for trapping target compounds chosen from monocyclic aromatic compounds, aldehydes, alkanes, carboxylic acids and ketones, and especially monocyclic aromatic compounds, aldehydes, alkanes, carboxylic acids and ketones, using as sensor a sol-gel material described above incorporating a probe molecule, in which a stream that may contain a target compound from among those mentioned previously is placed in contact with said sol-gel material described above incorporating a probe molecule, or such a stream is made to circulate thereon.

The stream may correspond to a gas that may contain these target compounds which may originate from a polluted atmosphere. The gaseous stream may circulate at a throughput ranging from 10 mL·min$^{-1}$ to 1.1 L·min$^{-1}$.

In addition to trapping these target compounds, they may also be detected and/or assayed. To this end, trapping of these molecules may also be performed.

A subject of the present patent application is thus also an above process in which, in addition, the detection of the target compounds trapped on the above sol-gel materials incorporating a probe molecule is performed.

The detection may especially be performed via optical, mass or acoustic measurements.

When the detection is performed via optical measurement, the wavelength for which the absorbance, fluorescence or luminescence of the probe molecule, or of the product formed by the interaction or reaction between the probe molecule and the target compounds, is the highest is preferably chosen.

To assay the target compounds trapped on the above sol-gel materials incorporating a probe molecule, it is especially possible to measure either the variations in absorbance, fluorescence or luminescence of the probe molecule over time or the variations in absorbance, fluorescence or luminescence of the product of the reaction between the probe molecule and the target pollutant over time. In both cases, the results will be compared with results obtained under the same exposure conditions with calibrated streams of target compounds.

A subject of the present patent application is also a system for trapping monocyclic aromatic hydrocarbons or an above target compound using, as sensor, a sol-gel material described above, optionally incorporating a probe molecule. Such a sensor usually comprises a block of sol-gel material described above of reproducible shape, for example parallelepipedal, cylindrical, cubic, trapezoidal, etc. shape, with a surface area of less than or equal to 150 mm$^2$ and preferably less than or equal to 100 mm$^2$, and with a thickness of less than or equal to 2 mm. This sensor is usually used in a cell essentially comprising:
- a millifluidic system for gaseous flow, in which is inserted a sol-gel material described above;
- an exposure chamber equipped with optical windows and apertures for the millifluidic system (gas inlet and outlet).

In the present specification, the term "millifluidic system" denotes a system for passing a gaseous stream at a throughput of 10 mL·min$^{-1}$ to 1.1 L·min$^{-1}$ and preferably 100 mL·min$^{-1}$ for the trapping step.

A subject of the present patent application is also a system for detecting monocyclic aromatic hydrocarbons and common solvents therefor using, as sensor, a sol-gel material described above, optionally incorporating a probe molecule. Such a detection system usually comprises:
- an above exposure chamber;
- an above millifluidic system;
- an optical system for collimating and focusing the analysis light;
- optical fibers for conveying the light;
- a (micro)pump suited to the desired throughput;
- a spectrophotometer or another detection device.

The detection system may especially be used as follows:

The block of sol-gel material is inserted in the millifluidic system. This system is placed in the exposure chamber. The mixture of gaseous target compounds is circulated in the millifluidic system for a short time (15 seconds to 2 minutes). During the exposure time, the absorption spectrum of the sensor is collected every second as described hereinbelow. The analysis light originating from a UV lamp (deuterium) is conveyed using an optical fiber and continuously illuminates the entry window of the chamber. The light beam, collimated using a lens (focal length=10 mm) and an SMA connector placed on the entry window, illuminates the sensor over a small surface area, for example 1 mm$^2$. The transmitted light is collected in the same axis via a second lens and a second SMA connector placed on the outlet window of the chamber. The transmitted light beam is conveyed using an optical fiber to a spectrophotometer, which is optionally miniature. An absorption spectrum of the sensor is collected every second, each acquisition lasting from 8 to 1000 msec (preferentially 20 msec).

When the acquisition is complete, the trapped target compounds may be released and the sensor purged. To this end, the sensor may be exposed to a stream of 4 L·min$^{-1}$ of air for about 5 minutes.

The absorbance signal of the sensor exposed to each target compound is acquired over a broad concentration range of the target compound and over a broad relative humidity range of the gaseous mixture. From these data, calibration curves are established for each target compound as a function of its concentration and of the humidity of the gaseous mixture. These calibration curves are stored in a databank that will serve for the spectral deconvolution of a spectrum of the sensor exposed to an unknown mixture of target compounds in gaseous form.

The absorbance signal is deconvoluted using a databank of absorption spectra of each of the target compounds determined previously in a matrix as described previously.

For the release step, the throughput of the gaseous stream may range from 2 L·min$^{-1}$ to 5 L·min$^{-1}$ and is preferably set at 4 L·min$^{-1}$.

In the case of a matrix doped with probe molecules that are capable of reacting with the target compounds, the reaction between the probe molecule and the target compound is irreversible in the majority of cases. The purging step is not performed to achieve release, but to purge the fluid circuit of the compounds present in the gaseous mixture that have not reacted with the probe molecules. In this case, the throughput of the purge stream will advantageously be set at a value of 10 mL·min$^{-1}$ to 1.1 L·min$^{-1}$.

In the case of a sol-gel material containing one or more probe molecules derived either from triphenylmethane or from azobenzene, the purging is advantageously performed by modifying the pH conditions of the stream or of the sol-gel material until a return to the initial optical measuring conditions is observed.

Moreover, when the fluid circuit functions continuously (or in a loop) by means of a circulation pump for a sufficiently long time (from a few seconds to 1 hour), during which the target compounds enter the matrix and react with the probe molecules, the optical measurements are taken (collection of absorption or of fluorescence spectra) at intervals that are preferably regular (1 to 300 seconds), during this period.

The examples that follow illustrate the present patent application and the invention will be understood more clearly with reference to the attached drawings, in which.

Figure 4A:
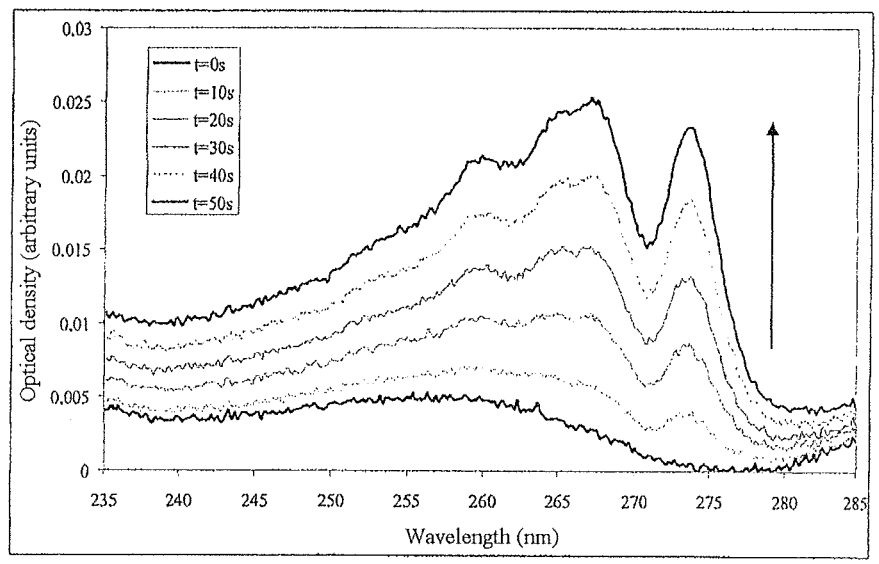
Figure 4B:
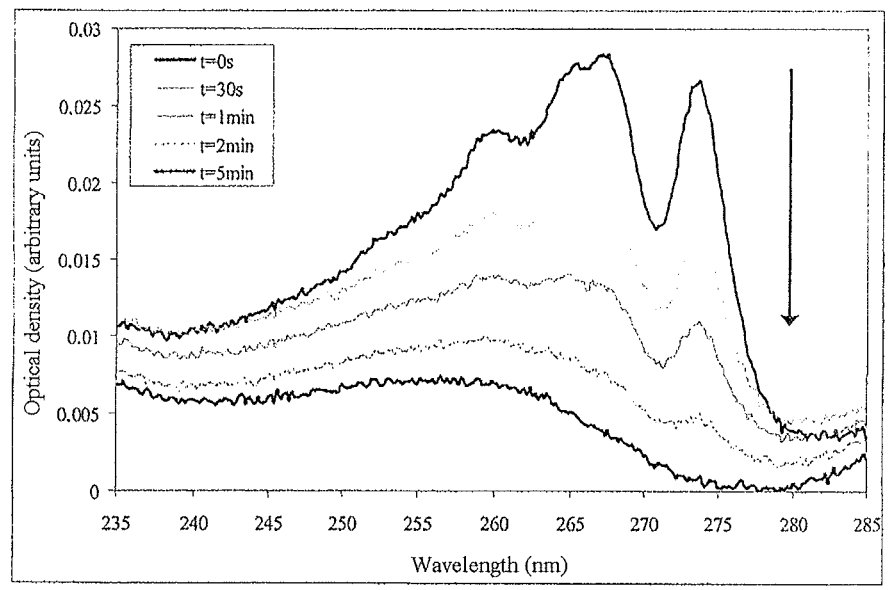
Figure 5:
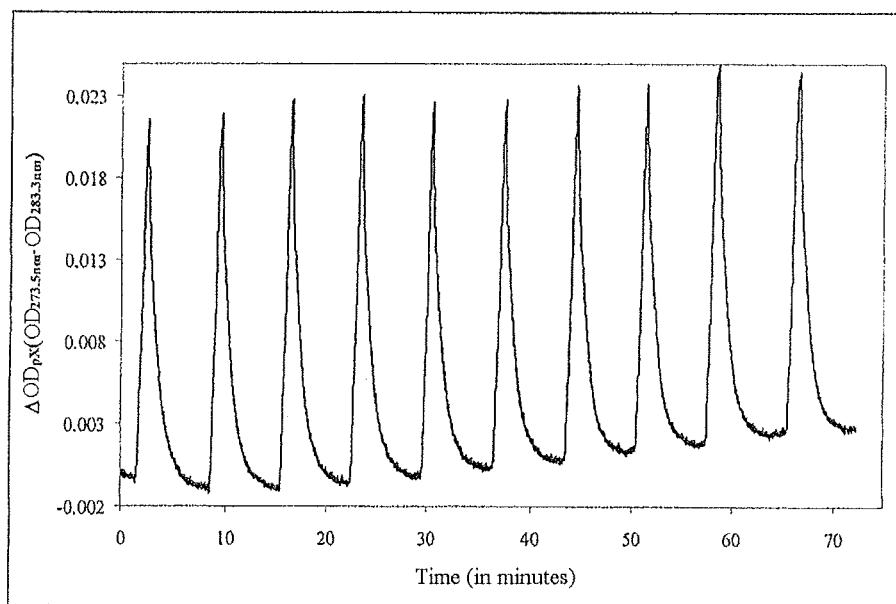
Figure 6:
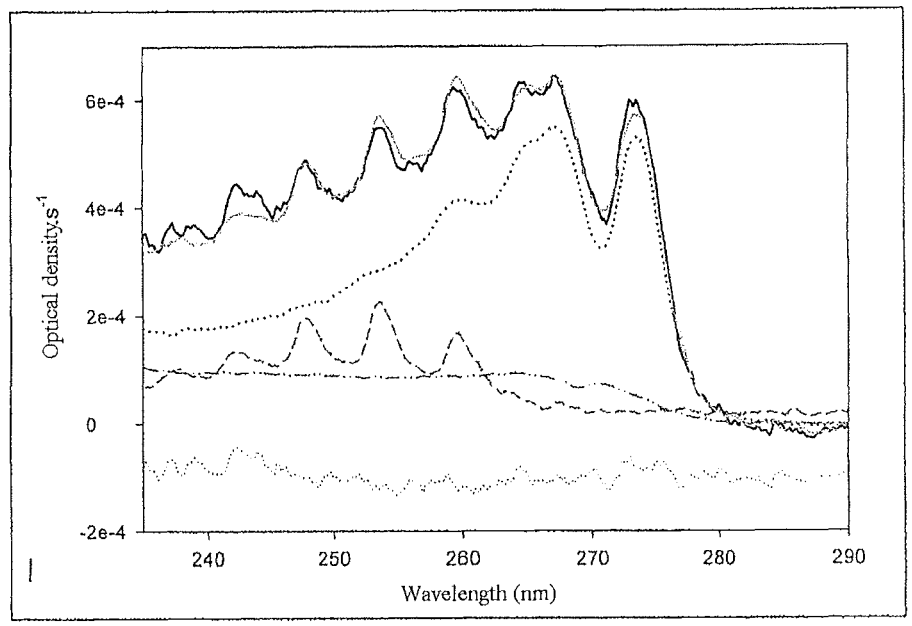
Figure 7A:
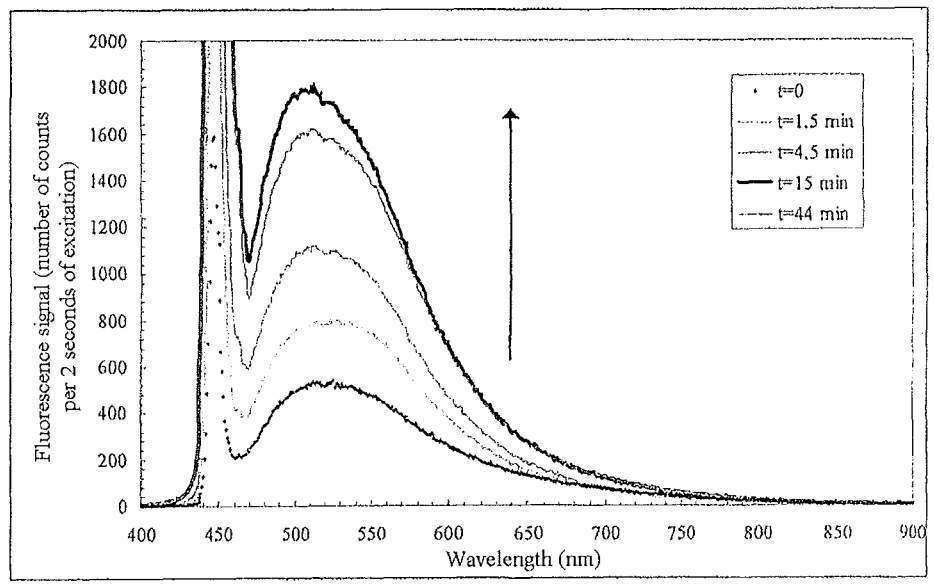
Figure 7B:
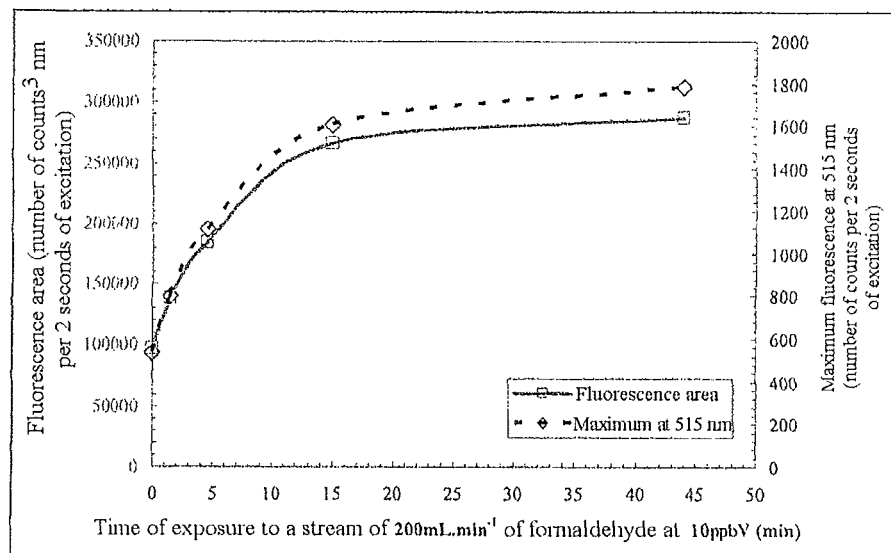
Figure 8A:
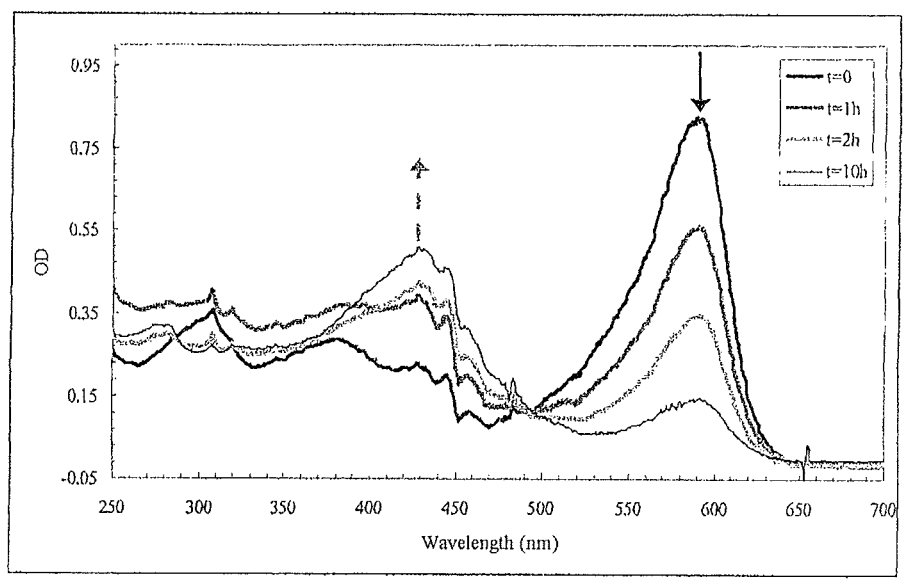
Figure 8B:
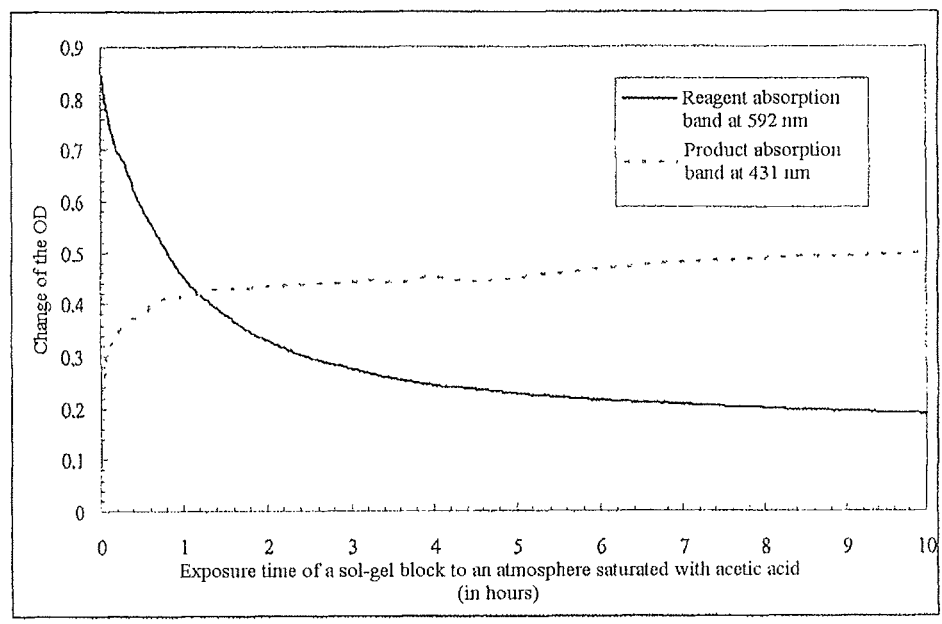

FIG. 4 shows the absorbance results for p-xylene as a function of the wavelength, for a sensor exposed to a stream of nitrogen containing 11.86 ppmv of p-xylene, in which FIG. 4a shows the change in absorption spectra of a target compound during trapping and FIG. 4b shows the change in absorption spectrum of a matrix during release (purging of the matrix in the case of simple trapping of the target compound by physical adsorption);

FIG. 5 shows a series of exposures of a sol-gel block to gaseous mixtures followed by purging of the sol-gel block. Each "pulse" corresponds to a linear increase in absorbance over one minute of exposure to a target compound, followed by an exponential decrease in absorbance for 5 minutes during purging. The value of the slope of the absorbance growth signal is characteristic of the concentration of the target compound in the exposure stream;

FIG. 6 is a spectrum recorded during an exposure to a mixture of target compounds (benzene, para-xylene and mesitylene). The spectrum corresponds to the sum of the spectra of the target compounds taken individually under the same conditions;

FIG. 7a shows the fluorescence spectra recorded during the exposure of a sol-gel block doped with probe molecules (in this case Fluoral-P®) to a gaseous stream of 200 mL·min$^{-1}$ containing 10 ppbv of formaldehyde. The spectral variations over time correspond to an increase in the fluorescence of the product derived from the reaction between the Fluoral-P® and the formaldehyde (excitation wavelength=405 nm–excitation time=2 seconds);

FIG. 7b shows the changes in fluorescence area (between 470 and 750 nm) on the one hand (solid-line curve) and in the maximum fluorescence at 520 nm (dashed-line curve) on the other hand, during the exposure of a matrix doped with Fluoral-P® to a stream of 200 mL·min$^{-1}$ containing 10 ppbv of formaldehyde. The slope at the origin of these two curves is characteristic of the concentration of formaldehyde in the exposure stream;

FIG. 8a shows the absorption spectra taken during the exposure of a sol-gel block doped with probe molecules (in this case bromophenol blue) to an atmosphere containing acetic acid at saturating vapor pressure. The spectral variations correspond, on the one hand, to a disappearance of the reagent (bromophenol blue, decrease in intensity of the absorption band at 592 nm) and, on the other hand, to a formation of the reaction product (appearance of an absorption band at 431 nm);

FIG. 8b shows the changes in optical density corresponding, on the one hand, to the disappearance of the reagent, bromophenol blue (solid-line curve) and to the appearance of the reaction product (protonated bromothymol blue), on the other hand, during the exposure of a block doped with bromophenol blue to an atmosphere containing acetic acid at saturating vapor pressure. The slope at the origin of these 2 curves is characteristic of the concentration of acetic acid in the exposure stream. This reaction is reversible by washing the monolith and desorption of the acetic acid.

EXAMPLE 1

Preparation of an APTES-TMOS Sol-Gel Block

Stage 1:

96-well polystyrene multiwell plates (Greiner Bio-one Elisa microplates flat bottom, ref. 655001) are heated in an oven at 50° C. for 24 hours, while degassing the oven three times during this period. This step degases the polystyrene molds to minimize the release of styrene monomer that might thereafter become trapped in the sol-gel material during the step of drying of the gel.

3.4 ml of tetramethoxysilane (TMOS, Fluka, ref. 87680) and 4.8 mL of methanol (Fluka, ref. 65540) are mixed using a magnetic stirrer for 2 minutes in a Pyrex beaker placed in a bath at −25° C. 0.2 mL of 3-amino-propyl)triethoxysilane (APTES, Fluka, ref. 09324) is then added to the mixture using a micropipette. After stirring for a further 2 minutes, 1.7 mL of Millipore ultrapure water are added. The mixture is stirred for a further 30 seconds. A sol is obtained, which is used as obtained in the following step.

Stage 2:

While maintaining the sol at −25±5° C. and working as quickly as possible, using a micropipette, 38 µL of sol are placed in each of the wells of a reference Greiner Bio-one Elisa microplate flat bottom plate (655101).

Stage 3:

Once the sol is gelled, the microwell plate is covered with a gas-permeable film (Gas permeable adhesive seals, ABGene, ref. AB-0718). The plate is placed in an oven at 40° C. for a duration of 2 hours. The plates are then removed from the oven and the matrices are stripped from the molds and placed in hermetic polypropylene dishes. The dishes are returned to the oven at 40° C. for 4 hours in order to complete the drying.

After drying, sol-gel blocks in the form of monolithic disks are obtained. The mean diameter of the sol-gel blocks obtained is 3.6 mm and their thickness is about 200±25 µm. Their mean specific surface area=750 m$^2$·g$^{-1}$. This was evaluated by establishing adsorption and desorption isotherms for nitrogen at the temperature of liquid nitrogen and by analyzing the isotherms using various analytical models proposed in the literature, such as the BET (Brunauer, Emmet and Taylor) model.

Their mean pore volume is 0.67 cm$^3$·g$^{-1}$. This was evaluated by establishing adsorption and desorption isotherms for nitrogen at the temperature of liquid nitrogen and by analyzing the isotherms using the DFT (density functional theory) analytical model.

The pore size distribution was evaluated by the DFT (density functional theory) method based on methods of calculating the interaction potential between the molecules of adsorbate and between the latter and the surface of the pores, which makes it possible to reconstitute macroscopic data such as the adsorption isotherm from the microscopic data such as the interaction potentials. The pore shape model ("spherical and cylindrical mixture") was used for the calculation.

The micropores are defined as pores with diameters≤20 Å.

The mesopores are defined as pores having diameters 20≤d≤500 Å.

The results obtained for the material of example 1 are as follows:
micropore/mesopore distribution (at the surface)=35/65%
micropore/mesopore distribution (in the bulk)=15/85%.

EXAMPLE 2

Preparation of an APTES-TMOS Sol-Gel Block

Various forms and sizes of matrices were prepared:
parallelepipedal (Star-Pack, ref. 47304 and ref. 271512 and ref. 303—Evergreen, ref. 201-3111-010)
cylindrical (Spex industries Inc., ref. 3111—Greiner Bio-one Elisa-microplates flat bottom, ref. 655001)
trapezoidal (Agar scientific, ref. G3533)
APTES-TMOS sol-gel blocks were prepared as in example 1 using Greiner Bio-one Elisa microplates flat bottom cylindrical molds (ref.: 655101), which gave blocks 3.6 mm in diameter and of variable thicknesses of between 80 and 1000 µm (as a function of the volume of the starting sol).

For each of the other molds referenced above and in the case of a material such as that of example 1, the final sol-gel block (i.e. after drying) conserves the shape of the mold, but its volume is about 8 times smaller than the starting volume. There is a shrinkage factor equal to 2 in the three dimensions on account of the expulsion of the residual solvents during the drying step.

EXAMPLE 3

Preparation of an APTES-TMOS Sol-Gel Block Incorporating a Probe Molecule

APTES-TMOS sol-gel blocks were prepared incorporating various probe molecules: 4-amino-3-penten-2-one (TCI, ref. A5350); bromophenol blue (Sigma-Aldrich, ref. 114391); methyl red (Sigma-Aldrich, ref. 250198); helianthin (Sigma-Aldrich, ref. 114510); Congo red (Aldrich, ref. 860956); bromocresol green (Sigma-Aldrich, ref. 114359) and bromocresol purple (Sigma-Aldrich, ref. 114375).

The incorporation of 4-amino-3-penten-2-one was performed according to three different processes described below:

"one-pot" doping: the process is performed as in example 1, but the methanol is replaced with a mixture of methanol+4-amino-3-penten-2-one. Various concentrations were used (100, 300, 500 and 750 mg of 4-amino-3-penten-2-one in 4.8 mL of methanol). The rest of the protocol is performed exactly as in example 1, except that in this case the drying of the sol-gel blocks is performed at 25° C.

"Liquid post-doping": sol-gel blocks such as those obtained in example 2 are dipped in an aqueous solution with a concentration of 4-amino-3-penten-2-one equal to $2\times10^{-3}$ mol·L$^{-1}$ for 2 hours and then dried under an inert gas.

"Gaseous post-doping": sol-gel blocks such as those obtained in example 2 are placed in a chamber under a reduced pressure of 133.3 Pa (1 torr) in the presence of powdered 4-amino-3-penten-2-one. The chamber is heated at 40° C. for 15 hours, during which the 4-amino-3-penten-2-one sublimes and penetrates into the sol-gel blocks, more specifically into the pores of the sol-gel blocks. At the end of the exposure, dry nitrogen is introduced into the chamber to reestablish atmospheric pressure and to recover the doped sol-gel blocks.

The incorporation of the other probe molecules mentioned previously (bromophenol blue; methyl red; helianthin; Congo red; bromocresol green and bromocresol purple) was performed solely via the "one-pot" doping method.

The process is performed as in example 1, but the methanol is replaced with a mixture of methanol and one of the compounds mentioned previously (bromophenol blue; methyl red; helianthin; Congo red; bromocresol green and bromocresol purple). Various concentrations were used, prepared from 0.5; 1; 10; 30; 50 and 100 mg dissolved in 4.8 mL of methanol. The rest of the protocol is performed exactly as in example 1, except that the drying of the sol-gel blocks is performed in a thermostatically regulated chamber at 25° C.

EXAMPLE 4

Preparation of a Millifluidic System

Figure 1:
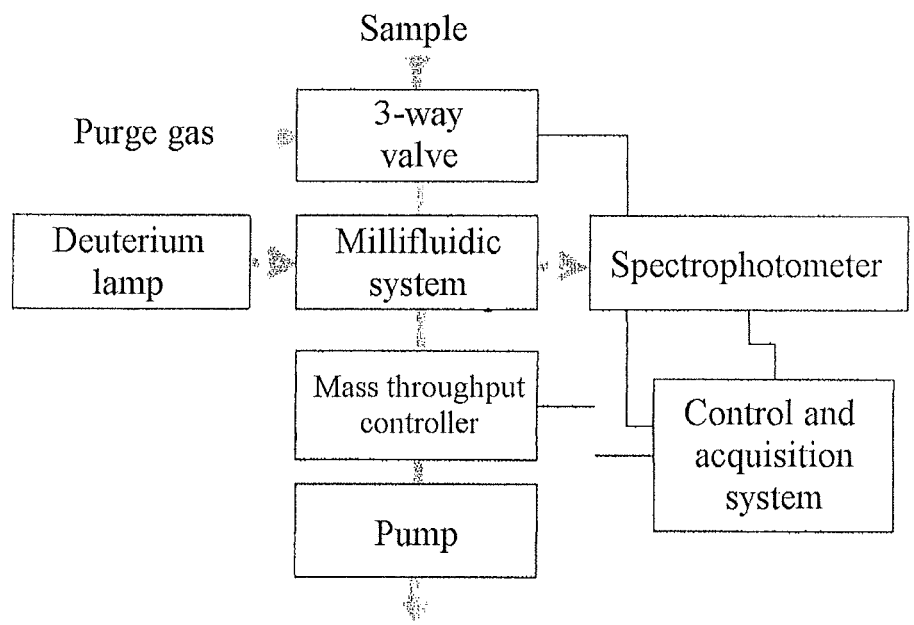
FIG. 1 is a diagrammatic view of the measuring device as a whole (measuring cell, spectrophotometer, deuterium lamp, pump)
Figure 2:
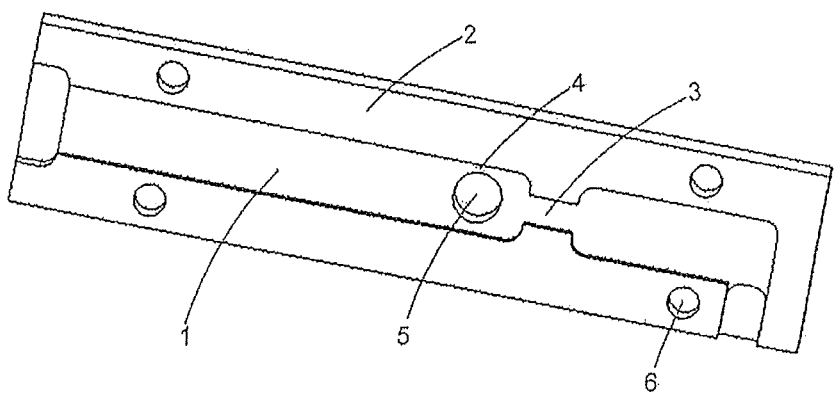
FIG. 2 is a view in perspective of one of the copper plates constituting the millifluidic system.

A millifluidic system was prepared, formed from two flat copper plates stuck together. The macrofluidic circuit 1 3.5 mm wide, 36 mm long and 0.5 mm deep was hollowed out in each copper plate 2 and during the assembly the two hollowed parts are stuck together. The millifluidic circuit 1 is L-shaped and comprises a narrowing 3 in the longest branch such that the width of the circuit there is only 1 mm (FIG. 2). A sol-gel block of example 2 was installed, and in another system a sol-gel block of example 3 just before the narrowing 3 at 4. The narrowing of the circuit allows good maintenance of the sol-gel disk. A hole 5 is made in the plates at the central position of the sol-gel block for passage of the analysis light beam. Other holes 6 were made to tighten the plates 2 together.

Millifluidic systems were also prepared with two PTFE plates 2, with two copper plates 2 and with two stainless steel plates 2.

EXAMPLE 5

Preparation of a Measuring Device

Figure 3:
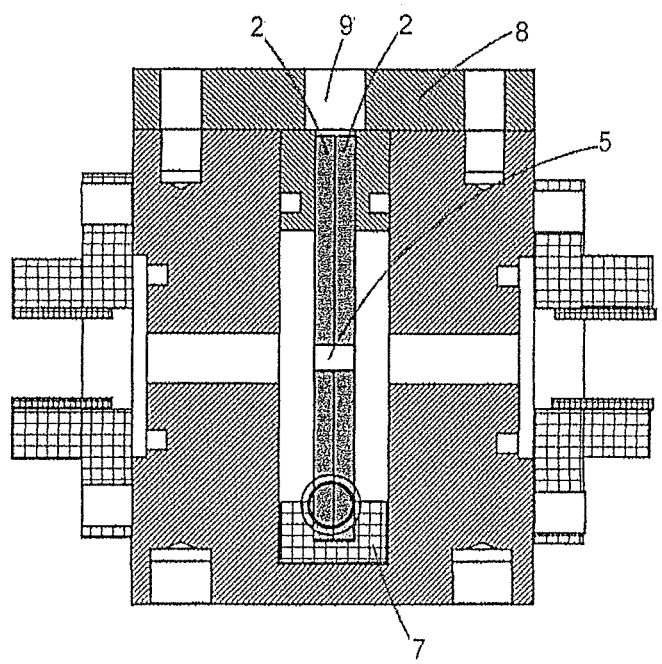
FIG. 3 is a view in cross section of an exposure chamber.

The copper assembly of example 4 was inserted into a PTFE measuring chamber equipped with two quartz optical windows (FIG. 3).

The exposure chamber comprises the millifluidic system. This system is held fixed in the exposure chamber by means of a base 7 provided for this purpose and a lid 8. In addition to maintaining the millifluidic system, the lid has a hole at its center 9 for passage of the gaseous mixture.

For the optical analysis of the sensor, the optical path of the analysis beam is perpendicular to the millifluidic system and passes through the center of the sensor formed by a sol-gel block of example 2 or, respectively, of example 3. Standard connectors for fibers (of SMA type) and lenses (focal length=10 mm) placed at the optical inlet and outlet of the exposure chamber allow collimation of the light beam conveyed by optical fibers at the inlet and outlet of the exposure chamber. On leaving the exposure chamber, the transmitted light beam is conveyed to a spectrophotometer (Ocean Optics, QE6500). An absorption spectrum of the sensor is collected, followed by exposing it to the stream of test product. From the start of exposure to the stream of the millifluidic system, and for a duration that may range between 30 seconds and 2 minutes in the case of a block of example 2 and between 1 and 120 minutes in the case of a block such as those of example 3, an absorption spectrum is collected every second and the data are stored for subsequent processing.

EXAMPLE 6

Trapping and Liberation of a Target Compound

An example of measurement of the exposure of a sensor to a stream of nitrogen containing 11.86 ppmv of p-xylene is shown in FIG. 5.

An APTES-TMOS sol-gel block obtained in example 2 was introduced into the millifluidic system of example 4 and the system of example 4 was placed in the measuring device of example 5.

A gaseous mixture containing 11.86 ppmv of para-xylene diluted in nitrogen was prepared.

This gaseous mixture was sent at a throughput of 100 mL·min$^{-1}$ into the above system for one minute. A stream of ambient air was then passed through the millifluidic circuit at a throughput of 4 L·min$^{-1}$ for 5 minutes.

From the start of introduction of the nitrogen stream containing p-xylene into the millifluidic circuit, spectra were collected every second. FIG. 4a shows the increase in the signal that corresponds to the absorbance of the trapped p-xylene, measured over a wavelength range from 235 to 285 nm. FIG. 4b shows the decrease in absorbance of p-xylene until a value corresponding to that measured before the exposure to p-xylene is reached.

The same type of experiments were also performed for different concentrations of gas (ranging from 0 to 120 ppmv) and for different types of gas (toluene, benzene, p-xylene, mesitylene) and under various relative humidity conditions (0 to 94%).

APPLICATION EXAMPLE 1

Measurement of a Target Compound without Humidity

The assay of p-xylene was performed by absorbance measurement as follows:

Prior to the assay of the p-xylene, a database of p-xylene absorption spectra in the sensor of example 2 was created.

A gaseous stream containing 11.86 ppmv of para-xylene diluted in nitrogen was prepared. The exposure throughput was set at 100 mL·min$^{-1}$.

The recording of a measurement took place in accordance with the following chronogram:
  insertion of the sol-gel block of example 2 in the assembly of example 4, which is itself placed in the device of example 5;
  purging of the device and stabilization of the lamp and of the spectrophotometer (Ocean Optics, QE65000) for 10 minutes;
  recording of the absorption spectrum of the sol-gel block;
  turning of the gas inlet valve to allow the exposure of the sol-gel block to the gaseous stream while recording one spectrum per second for one minute;
  turning of the valve to perform purging for 5 minutes with air.
  Each measuring cycle lasted 6 minutes on average.
  The humidity level was 0%.
  The results obtained are reported in FIG. 5.

It is observed that the response of the sensor is entirely reproducible. The measurement of the increase in the signal as a function of time (slope of the curve) gives repeatable values from one cycle to another with a very small standard deviation.

APPLICATION EXAMPLE 2

Measurement of a Target Compound in the Presence of Humidity

The process was performed as in application example 1, but the relative humidity level of the exposure stream was 80%.

The results obtained are reported in FIG. 6.

It is observed that the response of the sensor is entirely reproducible even with this high humidity level of the mixture. The measurement of the increase of the signal as a function of time (slope of the curve) gives repeatable values from one cycle to another, with a small standard deviation of 6.3%.

The sensor has a reproducible response in the relative humidity range examined from 0 to 94%.

APPLICATION EXAMPLE 3

Measurement of a Mixture of Target Compounds Without Humidity

The process was performed as in application example 1, but using a mixture containing 19.9 ppmv of benzene, 7.4 ppmv of mesitylene and 18.3 ppmv of p-xylene.

The results obtained are reported in FIG. 7.

The absorbance signal is deconvoluted from a databank of absorption spectra of the various target compounds in this device.

It is observed that the contents of target compounds extracted from the spectral deconvolution of the spectrum of the mixture of target compounds are very close to those in the mixture. Specifically, deconvolution gives a content of 19.6 ppmv of benzene, 17.3 ppmv of mesitylene and 17.2 ppmv of p-xylene.

It is concluded therefrom that the sensor satisfactorily captures all the monocyclic hydrocarbons, independently or as a mixture, with the same efficacy as when each of the target compounds is trapped separately.

APPLICATION EXAMPLE 4

Detection of a target compound with a matrix doped with 4-amino-3-penten-2-one by fluorescence measurement The assay of formaldehyde was performed by fluorescence measurement as follows:

Prior to the assay of the formaldehyde, a database of fluorescence spectra in a sensor of example 3 doped with 4-amino-3-penten-2-one (Fluoral-P®) via the "one-pot" method (500 mg in 4.8 mL of methanol) was created.

A gaseous stream containing 10 ppbv of formaldehyde diluted in dry air (FID grade, Messer, ref. 27880) was prepared. The exposure throughput was set at 200 mL·min$^{-1}$.

The recording of the measurements took place in accordance with the following chronogram:
  introduction of the sol-gel block of example 3 into the millifluidic system of example 4 and insertion of this assembly into the measuring device of example 5;
  purging of the device and stabilization of the excitation lamp and of the spectrophotometer (Ocean Optics, ref. QE65000) for 15 minutes;
  recording of the fluorescence spectrum of the sol-gel block;

turning of the inlet valve to allow exposure of the sol-gel block to the gaseous stream and recording of a fluorescence spectrum every 30 seconds (pre-excitation for 2 seconds) for 45 minutes.

The results are reported in FIGS. 7a and 7b.

APPLICATION EXAMPLE 5

Detection of a Target Compound with a Matrix Doped with Bromophenol Blue by Absorbance Measurement The experiment consisted in exposing a block of sol-gel of example 3 doped with bromophenol blue via the "one-pot" method (0.25 mg in 4.8 mL of methanol) in an atmosphere saturated with acetic acid (saturating vapor pressure under standard temperature and pressure conditions). The bromophenol blue reacts with the acetic acid that has diffused into the matrix to form a product whose absorption spectrum differs from that of the starting reagent (see FIG. 8a). In this case, the increase of the signal corresponding to the absorption of the product formed during the reaction (absorption band at 431 nm) as a function of the exposure time, and the decrease of the signal corresponding to the absorption of the reagent (band at 592 nm) as a function of the exposure time, were measured. These two values are directly proportional to the concentration of acetic acid. The results are presented in FIGS. 8a and 8b.

The invention claimed is:

1. A porous sol-gel material consisting essentially of:
   units of one or more first polyalkoxysilane(s) selected from the following compounds: (chloromethyl)triethoxysilane; 1,3-dimethyltetramethoxydisiloxane; ethyltrimethoxysilane; triethoxy(ethyl)silane; triethoxymethylsilane; triethoxy(vinyl)silane; trimethoxymethylsilane; trimethoxy(vinyl)silane; tetraethoxysilane and tetramethoxysilane (TMOS); and
   units of one or more second polyalkoxysilane(s) selected from the following compounds: (N-(3-(trimethoxysilyl)propyl)ethylenediamine; 3-amino-propyltriethoxysilane (APTES) and 3-aminopropyltrimethoxysilane in a first polyalkoxy-silane(s)/second polyalkoxysilane(s) mole ratio of 1/0.01 to 1/1; wherein the porous sol-gel matrix is solid, self-standing and transparent to UV radiation; and
   wherein the sol-gel material is prepared according to a process comprising:
   mixing the first polyalkoxysilane(s), at a temperature of −25 to −15° C., with a water-miscible organic solvent therefor, then
   adding a second polyalkoxysilane(s),
   adding water; and
   continuing stirring to obtain a sol and then the defined sol-gel.

2. A sol-gel material as claimed in claim 1, characterized in that the first polyalkoxysilane(s)/second polyalkoxysilane(s) mole ratio is from 1/0.01 to 1/0.30.

3. A sol-gel material as claimed in claim 1, characterized in that the first polyalkoxysilane(s) are chosen from the following compounds: methyltrimethoxysilane, tetraethoxysilane, methyltriethoxysilane and tetramethoxysilane (TMOS).

4. A sol-gel material as claimed in claim 1, wherein:
   the first polyalkoxysilane is limited to a single material from the defined list, or
   the first polyalkoxysilane is limited to a single material from the defined list and the second polyalkoxysilane is limited to a single material from the defined list.

5. A sol-gel material as claimed in claim 1, characterized in that the second polyalkoxysilane is 3-aminopropyltriethoxysilane.

6. A sol-gel material as claimed in claim 1, characterized in that it comprises a probe molecule.

7. A sol-gel material as claimed in claim 6, characterized in that the probe molecule is chosen from hydralazine, 4-amino-3-penten-2-one, 2,4-dinitrophenylhydrazine, iodine oxides, triphenylmethane derivatives, azobenzene derivatives and alkyl halides.

8. A process for preparing a sol-gel material as defined in claim 1, characterized in that the first polyalkoxysilane(s) are mixed, at a temperature of −25 to −15° C., with a water-miscible organic solvent therefor, the second polyalkoxysilane is then added, water is added, supplemented, if desired, with a catalyst or a structuring agent, or both, and stirring is continued to obtain the sol and then the expected sol-gel, which, if desired, is placed in sol form in molds to obtain expected sol-gel blocks.

9. A process as claimed in claim 8, characterized in that the mixing of the first polyalkoxysilane(s) with a water-miscible organic solvent therefor is performed for a time of between 1 and 10 minutes.

10. A process as claimed in claim 8, characterized in that the polyalkoxysilanes/solvent/water mole ratio is from 1/4/1 to 1/100/30.

11. A process for preparing a sol-gel material incorporating a probe molecule as defined in claim 8 characterized in that a probe molecule is added either directly during the preparation of the sol of the sol-gel material, or by diffusion of this probe molecule into the material via gas-phase or liquid-phase diffusion.

12. A process for trapping monocyclic aromatic hydrocarbons using, as sensor, a sol-gel material as defined in claim 1, in which a stream that may contain monocyclic aromatic hydrocarbons is placed in contact with the sol-gel material, optionally incorporating a probe molecule, or such a stream is made to circulate thereon.

13. A process as claimed in claim 12, characterized in that the detection of the monocyclic aromatic hydrocarbons trapped on the sol-gel materials optionally incorporating a probe molecule is also performed.

14. A process for trapping pollutants chosen from aldehydes, aromatic compounds, alkanes, carboxylic acids, ketones and chlorine using as sensor a sol-gel material as defined in claim 1, incorporating a probe molecule, in which a stream that may contain a pollutant from among those mentioned above is placed in contact with said sol-gel material incorporating a probe molecule, or such a stream is made to circulate thereon.

15. A system for trapping or detecting monocyclic aromatic hydrocarbons or a pollutant using as sensor a sol-gel material as defined in claim 1, optionally incorporating a probe molecule.

16. A sol-gel material according to claim 1, wherein the pores of said porous sol-gel material have a pH of from 7 to 8.2.

17. A sol-gel material according to claim 1 wherein, in the water addition step, the water is supplemented with a catalyst, a structuring agent, or both.

18. A porous sol-gel material consisting essentially of:
   units of one or more first polyalkoxysilane(s) selected from the following compounds: (chloromethyl)triethoxysilane; 1,3-dimethyltetramethoxydisiloxane; ethyltrimethoxysilane; triethoxy(ethyl)silane; triethoxymethylsilane; triethoxy(vinyl)silane;

trimethoxymethylsilane; trimethoxy(vinyl)silane; tetraethoxysilane or tetramethoxysilane (TMOS); and units of one or more second polyalkoxysilane(s) selected from the following compounds: (N-(3-(trimethoxysilyl) propyl)ethylenediamine; 3-amino-propyltriethoxysilane (APTES) and 3-aminopropyltrimethoxysilane, in a first polyalkoxy-silane(s)/second polyalkoxysilane(s) mole ratio of 1/0.01 to 1/1; wherein the porous sol-gel matrix is solid, self-standing and transparent to UV radiation, wherein said porous sol-gel material is prepared according to the process comprising:

mixing the first polyalkoxysilane(s), at a temperature of −25 to −15° C., with a water-miscible organic solvent therefor, then adding a second polyalkoxysilane(s), adding water, and continuing stirring to obtain a sol, placing the sol in a mold, and obtaining a solid, self-standing and transparent to UV radiation block of the defined sol-gel.

19. A sol-gel material according to claim 18 wherein, in the water addition step, the water is supplemented with a catalyst, a structuring agent, or both.

20. A sol-gel material as claimed in claim 18, characterized in that the first polyalkoxysilane(s)/second polyalkoxysilane (s) mole ratio is from 1/0.01 to 1/0.30.

21. A sol-gel material as claimed in claim 18, characterized in that the first polyalkoxysilane(s) are chosen from the following compounds: methyltrimethoxysilane, tetraethoxysilane, methyltriethoxysilane and tetramethoxysilane (TMOS).

22. A sol-gel material as claimed in claim 18, wherein:

the first polyalkoxysilane is limited to a single material from the defined list, or the first polyalkoxysilane is limited to a single material from the defined list and the second polyalkoxysilane is limited to a single material from the defined list.

23. A sol-gel material as claimed in claim 18, characterized in that the second polyalkoxysilane is 3-aminopropyltriethoxysilane.

24. A sol-gel material as claimed in claim 18, characterized in that it comprises a probe molecule.

25. A sol-gel material as claimed in claim 24, characterized in that the probe molecule is chosen from hydralazine, 4-amino-3-penten-2-one, 2,4-dinitrophenylhydrazine, iodine oxides, triphenylmethane derivatives, azobenzene derivatives and alkyl halides.

26. A process for preparing a sol-gel material as defined in claim 18, characterized in that the first polyalkoxysilane(s) are mixed, at a temperature of −25 to −15° C., with a water-miscible organic solvent therefor, the second polyalkoxysilane is then added, water is added, supplemented, if desired, with a catalyst or a structuring agent, or both, and stirring is continued to obtain the sol and then the expected sol-gel, which, if desired, is placed in sol form in molds to obtain expected sol-gel blocks.

27. A process as claimed in claim 26, characterized in that the mixing of the first polyalkoxysilane(s) with a water-miscible organic solvent therefor is performed for a time of between 1 and 10 minutes.

28. A process as claimed in claim 26, characterized in that the polyalkoxysilanes/solvent/water mole ratio is from 1/4/1 to 1/100/30.

29. A process for preparing a sol-gel material incorporating a probe molecule as defined in claim 26, characterized in that a probe molecule is added either directly during the preparation of the sol of the sol-gel material, or by diffusion of this probe molecule into the material via gas-phase or liquid-phase diffusion.

30. A process for trapping monocyclic aromatic hydrocarbons using, as sensor, a sol-gel material as defined in claim 18, in which a stream that may contain monocyclic aromatic hydrocarbons is placed in contact with the sol-gel material, optionally incorporating a probe molecule, or such a stream is made to circulate thereon.

31. A process as claimed in claim 30, characterized in that the detection of the monocyclic aromatic hydrocarbons trapped on the sol-gel materials optionally incorporating a probe molecule is also performed.

32. A process for trapping pollutants chosen from aldehydes, aromatic compounds, alkanes, carboxylic acids, ketones and chlorine using as sensor a sol-gel material as defined in claim 18, incorporating a probe molecule, in which a stream that may contain a pollutant from among those mentioned above is placed in contact with said sol-gel material incorporating a probe molecule, or such a stream is made to circulate thereon.

33. A system for trapping or detecting monocyclic aromatic hydrocarbons or a pollutant using as sensor a sol-gel material as defined in claim 18, optionally incorporating a probe molecule.

34. A sol-gel material according to claim 18, wherein the pores of said porous sol-gel material have a pH of from 7 to 8.2.

* * * * *